(12) United States Patent
Warner

(10) Patent No.: US 9,446,060 B2
(45) Date of Patent: Sep. 20, 2016

(54) METHOD OF PRODUCING THERAPEUTIC AGENT

(71) Applicant: Deborah Warner, Houston, TX (US)

(72) Inventor: Deborah Warner, Houston, TX (US)

( * ) Notice: Subject to any disclaimer, the term of this patent is extended or adjusted under 35 U.S.C. 154(b) by 0 days.

(21) Appl. No.: 14/933,328

(22) Filed: Nov. 5, 2015

(65) Prior Publication Data

US 2016/0058778 A1  Mar. 3, 2016

Related U.S. Application Data

(63) Continuation-in-part of application No. 14/249,837, filed on Apr. 10, 2014, now abandoned.

(51) Int. Cl.
| | |
|---|---|
| *C07C 229/00* | (2006.01) |
| *A61K 31/675* | (2006.01) |
| *A61K 31/205* | (2006.01) |
| *A61K 31/194* | (2006.01) |
| *C07C 227/42* | (2006.01) |
| *C07C 51/43* | (2006.01) |

(52) U.S. Cl.
CPC ........... *A61K 31/675* (2013.01); *A61K 31/194* (2013.01); *A61K 31/205* (2013.01); *C07C 51/43* (2013.01); *C07C 227/42* (2013.01); *C07B 2200/13* (2013.01)

(58) Field of Classification Search
CPC ............. A61K 31/675; A61K 31/194; A61K 31/302; A61K 31/205; C07C 227/42; C07C 51/43; C07C 229/70; C07C 59/255; C07B 2200/13

See application file for complete search history.

(56) References Cited

U.S. PATENT DOCUMENTS

2014/0316156 A1 * 10/2014 Warner .................. C07C 51/43
560/176

* cited by examiner

*Primary Examiner* — Yevegeny Valenrod
*Assistant Examiner* — Blaine G Doletski
(74) *Attorney, Agent, or Firm* — Berry Choobin; Patent 360

(57) ABSTRACT

The present invention relates to a therapeutic agent, wherein the therapeutic agent is D-Boramine. The therapeutic agent is prepared by mixing L-carnitine tartrate, pyridoxal 5' phosphate and fumaric acid. D-Boramine, when administered orally or parenterally in therapeutic quantities, is effective for use in the prevention of cancer that arises from mutations to the BRCA1 and BRCA2 genes, i.e., breast and ovarian and the treatment of several types of human diseases including, but not limited to, Antiphospholipid Syndrome, Disseminate Intravascular Coagulation (DIC), infections arising from viruses (including strains of Human Papillomavirus, Herpes Simplex Virus and Simian Virus), tuberculosis (including XDR Tuberculosis) and mycoplasma, Hepatitis A, B and C, MTHFR genetic mutations.

9 Claims, No Drawings

METHOD OF PRODUCING THERAPEUTIC AGENT

CROSS-REFERENCE TO RELATED APPLICATIONS

The present application is a CIP of U.S. Non-Provisional Application Ser. No. 14/249,837 which claims priority to Provisional application No. 61/813,403 for Method of Producing Therapeutic Agent that was filed on Apr. 18, 2013.

BACKGROUND

1. Technical Field of the Invention

The present invention relates to a method of producing a therapeutic agent for use in the prevention of cancer that arises from mutations to the BRCA1 and BRCA2 genes, i.e., breast and ovarian, and the treatment of several types of human diseases including, but not limited to, Antiphospholipid Syndrome, Disseminate Intravascular Coagulation (DIC), infections arising from viruses (including strains of Human Papillomavirus (HPV), Herpes Simplex Virus (HSV), Simian Virus (SV), tuberculosis (including XDR Tuberculosis) and mycoplasma, Hepatitis A, B and C, MTHFR genetic mutations.

The agent works at the cellular level. In some cases it enables cells to mount an effective defense against infectious agents and has also effected the restoration of proper protein morphology, protein folding, and epigenetic signaling for damaged BRCA1, BRCA2 and MTHFR genes. In other cases, it acts to prevent BRCA1 and BRCA2 mutations from developing oncogenic cells. This represents an entirely new front in the battle against BRCA1 and BRCA2 related cancers.

The technical field of the invention is a formulation that acts on human cells with nutraceutical, pharmaceutical, genetic repair and epigenetic repair modes of action.

2. Description of the Related Art

A variety of therapeutic agents have been employed to treat or prevent the conditions cited above. Some attack invasive or infectious microbes while some directly attack diseased human cells. These agents often require complex synthesis methods or have a risky dosing scheme and method of administration. Still, few of these agents are effective and fewer act at the cellular level in a manner that enables them to break biofilms or mount an effective counterattack to these invaders or to correct any related genetic mutations.

The field of epigenetics is now key in the research and development of therapies to address pathology in the cells of living organisms. Great strides have been made now that we have an increased understanding of various epigenetic mechanisms, like histone modification, DNA methylation and small non-coding RNAs.

Research has documented that mutations affecting the DNA Damage Recovery Pathways often lead to mutations in genes as well as to alterations in epigenetic signaling of genes including BRCA1, BRCA2 and MTHFR. Together, these mutations and signaling abnormalities turn off apoptosis signals or turn on senescence signals that leave these cells susceptible to mutation, infection, and toxins. Current genetic scanning technology detects these cellular conditions as abnormal gene sequences, single nucleotide polymorphisms, abnormal morphologies and abnormal protein folding patterns.

In some cases these mutations are somatic cell abnormalities only, and their resolution resolves the present disease condition. However, some mutations are germ-line mutations that, if not corrected, will be inherited by future generations.

In the case of viral infections, many attempts have been made at producing vaccines, with limited success. In the case of HPV, HSV, SV and viral Hepatitis, few agents are effective at halting the progression of an active infection and none are known to succeed at destroying the virus in the cell.

Carnitine plays a key role in fatty acid oxidation. Because of this role, there is interest as to whether carnitine D-Boramine has been proven to be beneficial in genetic or acquired disorders of energy production to improve fatty acid oxidation, to remove accumulated toxic fatty acyl-CoA metabolites, or to restore the balance between free and acyl-CoA. There are two known disorders in children where the carnitine supply becomes limiting for fatty acid oxidation, and supplementation with carnitine is essential. The first disorder is a recessive genetic defect of the muscle/kidney sodium-dependent, plasma membrane carnitine transporter, which presents as cardiomyopathy or hypoketotic hypoglycemia in infancy. The second disorder arises from chronic administration of pivalate conjugated antibiotics, in which excretion of pivaloyl-carnitine can result in carnitine depletion. In the latter situation, tissue levels may become low enough to limit fatty acid oxidation. The benefits of carnitine supplementation in secondary carnitine deficiencies may require invasive endurance studies of fasting ketogenesis or muscle and cardiovascular work, as carnitine becomes rate limiting only at very low concentrations.

Hence there is a need to develop a therapeutic agent that is effective in the prevention of cancers arising from BRCA1 and BRCA2 genetic mutations, and in the treatment of viral infections, cancers, tuberculosis, and other diseases, and to repair disorders arising from carnitine deficiency. There is a need to provide a therapeutic agent that can enter both somatic and germ-line cells, and enable the mitochondria to repair these defects and restore a non-mutated homeostasis to the cell and its intra-cellular signaling.

There is also a need to come up with a simple method of preparing a therapeutic agent and administering it.

The above-mentioned shortcomings, disadvantages and problems are addressed herein as detailed below.

SUMMARY OF THE INVENTION

The primary object of the present invention is to provide a therapeutic agent for the prevention and treatment of cancer, viral and mycoplasma infections and other diseased conditions.

Another object of the present invention is to provide a method of preparing the therapeutic agent.

The present invention is a method for treating viral and mycoplasma infections, cancers, and other diseases and correcting both somatic and germ-line genetic mutations by administering a therapeutic agent and the agent thus produced.

According to the preferred embodiment of the invention, this therapeutic agent, referred to as D-Boramine, is formulated by preparing a dry admixture of L-carnitine tartrate [CAS 36687-82-8], pyridoxal-5'-phosphate [CAS 54-47-7] and fumaric acid [CAS 110-17-8]. The therapeutic agent's effectiveness for a specific disease condition or infectious agent is tuned by adjusting the relative proportions by weight of each ingredient across a broad range that includes:

L-carnitine tartrate: 34-90%,
pyridoxal-5'-phosphate: 5-33%, and
fumaric acid 0.5-33%.

D-Boramine has been shown to be useful as a therapeutic agent in treating a variety of viral diseases, cancers, and other diseases and in permanent correction of certain regulatory genetic mutations to somatic and germ-line cells including, but not limited to, mutations of the BRCA1 and BRCA2 genes.

The disease of viral origin is selected from the group consisting of Human Papillomavirus (all strains), Herpes Simplex Virus (Strains 1, 2, and 6), Simian Virus (Strains 5 and 40), and Hepatitis (Types A, B, and C).

The cancer is selected from the group including breast, ovarian, Non-Hodgkin's Lymphoma, B-Cell Lymphoma, prostate, pancreatic, melanoma and other cancers arising from mutations to genes (BRCA1, BRCA2, and MTHFR) and the related change of genetic cell signals.

The other disease condition is selected from the group consisting of Antiphospholipid Syndrome, DIC (Disseminated Intravascular Syndrome) and Carnitine Deficiency Disorders, Tuberculosis, XDR Tuberculosis and mycoplasma.

Other embodiments of the invention may be produced by substituting in place of L-carnitine tartrate, other biochemically equivalent forms of L-carnitine including, but not limited to, acetyl-L-carnitine and various L-carnitine salts, including the tartrate, fumarate, and magnesium citrate forms.

Other embodiments of the invention may be produced by substituting in place of pyridoxal-5'-phosphate, other forms of Vitamin B-6 that metabolize in the human body into pyridoxal-5'-phosphate including, but not limited to, pyridoxol, pyridoxine, pyridoxine hydrochloride and pyridoxamine.

The method of preparing other embodiments by substituting for the ingredients in the preferred embodiment may require adjustment of the relative amounts of each ingredient but remaining within the range specified above.

Powdered D-Boramine may be placed into soft gels for oral administration or may be dissolved in sterile water and administered orally or parenterally.

DETAILED DESCRIPTION OF THE PREFERRED EMBODIMENT

The embodiments are described in sufficient detail to enable those skilled in the art to practice the embodiments, and it is to be understood that the logical, mechanical and other changes may be made without departing from the scope of the embodiments. The following detailed description is therefore not to be taken in a limiting sense.

D-Boramine, the therapeutic agent, is prepared in a low humidity environment, taking special caution to prevent exposing the ingredients to water or water vapor. The steps include placing each ingredient in a clean, dry container, and then stirring to obtain a uniform admixture. The ingredients include 34% to 90% by weight of L-carnitine tartrate (or one of the substituted compounds described above), 5% to 33% by weight of pyridoxal-5'-phosphate (or one of the substituted compounds described above) and 0.5% to 33% by weight of fumaric acid.

In the clinic, DNA analysis is used to determine the disease condition to be treated, and cellular response testing is used to determine the therapeutically effective dose and to select the method of administration.

D-Boramine is used therapeutically in doses ranging from 100 mg to 8,000 mg. The dosage is dependent upon the cell response testing. The D-Boramine is administered orally in capsule or liquid form or is administered intravenously in liquid form. D-Boramine may be dissolved into purified water for oral administration and into normal saline or sterile water to permit intravenous administration using a 0.22 micron filter, as desired.

In the specific cases of cancer or cancer prevention resulting from mutations to BRCA1, BRCA2 and MTHFR genes, genetic analysis determines that one or more of these genes are in a mutated state prior to treatment with D-Boramine. After clinical tests indicate that the patient's cancer has been arrested, a genetic analysis is performed and confirms that the genes are no longer in a mutated state but have been restored to a normal composition, morphology, protein folding sequence and epigenetic signaling.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification but is to be limited only by the scope of the attached claim or claims, including the full range of equivalency to which each element thereof is entitled.

What is claimed:

1. A method for producing a therapeutic agent used for treatment of disease of viral origin, to prevent and treat cancer and other diseased conditions, said method comprising the step of:
   Preparing a dry admixture of L-carnitine tartrate, pyridoxal-5'-phosphate and fumaric acid to obtain a therapeutic agent; and administering orally or parenterally a therapeutically effective amount of the agent.

2. The method according to claim 1, wherein an amount of L-carnitine tartrate added is 34% to 90% by weight of the composition.

3. The method according to claim 1, wherein an amount of pyridoxal-5'-phosphate added is 5% to 33% by weight of the composition.

4. The method according to claim 1, wherein an amount of fumaric acid added is 0.5% to 33% by weight of the composition.

5. The method according to claim 1, wherein the therapeutic agent is D-Boramine.

6. The method according to claim 1, wherein the disease of viral origin is selected from the group consisting of Human Papillomavirus (all strains), Herpes Simplex Virus (Strains 1, 2 and 6), Simian Virus (Strains 5 and 40), and Hepatitis (A, B, and C).

7. The method according to claim 1, wherein the cancer to be prevented or treated is selected from the group consisting of Non-Hodgkin's Lymphoma, B-cell Lymphoma, ovarian, breast and prostate and melanoma cancers arising from mutations to genes including BRCAI, BRCA2 and MTHFR or from changes in genetic cell signaling arising from these mutations.

8. The method according to claim 7, where genetic analysis determines that previously mutated genes from the group BRCAI, BRCA2 and MTHFR have been reset by D-Boramine therapy to a normal, non-mutated morphology and folding sequence with an accompanying return to normal genetic signaling.

9. The method according to claim 1, wherein the other disease condition is selected from the group consisting of Antiphospholipid Syndrome, DIC, tuberculosis, XDR Tuberculosis andmycoplasma.

* * * * *